United States Patent [19]
Lader et al.

[11] Patent Number: 6,057,134
[45] Date of Patent: May 2, 2000

[54] MODULATING THE EFFICIENCY OF NUCLEIC ACID AMPLIFICATION REACTIONS WITH 3' MODIFIED OLIGONUCLEOTIDES

[75] Inventors: Eric S. Lader; Marianna Goldrick; Matthew Winkler, all of Austin, Tex.

[73] Assignee: Ambion, Inc., Austin, Tex.

[21] Appl. No.: 08/726,519

[22] Filed: Oct. 7, 1996

[51] Int. Cl.$^7$ .......................... C12P 19/34; C07H 21/04; C07H 21/00
[52] U.S. Cl. .................. 435/91.2; 435/91.1; 536/22.1; 536/23.1; 536/25.32
[58] Field of Search ................... 435/91.2, 91.1; 536/23.1, 25.32, 22.1

[56] References Cited

U.S. PATENT DOCUMENTS

| | | | |
|---|---|---|---|
| 5,348,853 | 9/1994 | Wang et al. | 435/6 |
| 5,545,540 | 8/1996 | Mian | 435/91.2 |
| 5,567,583 | 10/1996 | Wang et al. | 435/6 |

FOREIGN PATENT DOCUMENTS

WO 94/03472  2/1994  WIPO.

OTHER PUBLICATIONS

Compton, "Nucleic Acid Sequence–Based Amplification," *Nature*, 350:91–92, 1991.

Gaudette and Crain, "A Simple Method for Quantifying Specific mRNAs in Small Numbers of Early Mouse Embryos," *Nucleic Acids Research*, 19(8):1879–1884, 1991.

Guatelli et al., "Isothermal in Vitro Amplification of Nucleic Acids by a Multienzyme Reaction Modeled After Retroviral Replication," *PNAS*, 87:1874–1878, 1990.

Holland et al., "Detection of Specific Polymerase Chain Reaction Product by Utilizing the 5'–>3' Exonuclease Activity of *Thermus Aquaticus* DNA Polymerase," *Proc. Natl. Acad. Sci. USA*, 88:7276–7280, 1991.

Horikoshi et al., "Qunatitation of Thymidylate Synthesis, Dihydrofolate Reductase, and DT–Diaphoreses Gene Expression in Human Tumors Using the Polymerase Chain Reaction," *Cancer Research*, 52:108–116, 1992.

Lee et al., "Allelic Discrimination by Nick–Translation PCR™ with Fluorogenic Probes," *Nucl. Acids. Research*, 21:3761–3766, 1993.

Nicoletti and Sassy–Prigent, "An Alternative Quantitative Polymerase Chain Reaction Method," *Anal Biochem*, 236:229–241, 1996.

Orum et al., "Single Base Pair Mutation Analysis by PNA Directed PCR Clamping," *Nucl. Acids Research*, 21(23):5331–5336, 1993.

Wong et al., "Monitoring mRNA Expression by Polymerase Chain Reaction: The 'Primer–Dropping' Method," *Annal Biochem.*, 223:251–258, 1994.

*Primary Examiner*—Ardin H. Marschel
*Assistant Examiner*—Joyce Tung
*Attorney, Agent, or Firm*—Arnold White & Durkee

[57] ABSTRACT

The invention relates to modified oligonucleotide primers used to adjust the amplification efficiency of an abundant target without affecting the amplification of other targets in a DNA synthesis reaction. The invention may be used in PCR™ or any other primer dependent DNA transcription technology.

17 Claims, 2 Drawing Sheets

FIG. 1

18S PCR primers

5´ TCA AGA ACG AAA GTC GGA GG -OH 3´    (SEQ ID NO:1)
    5´ GGA CAT CTA AGG GCA TCA CA -OH 3´    (SEQ ID NO:2)

18S Blocked primers

5´ TCA AGA ACG AAA GTC GGA GG -OPO$_3$ 3´    (SEQ ID NO:3)
    5´ GGA CAT CTA AGG GCA TCA CA -OPO$_3$ 3´    (SEQ ID NO:4)

Cyclophilin PCR primers

5´ CCA TCG TGT CAT CAA GGA CTT CAT 3´    (SEQ ID NO:5)
    5´ CTT GCC ATC CAG CCA GGA GGT CTT 3´    (SEQ ID NO:6)

MODULATING THE EFFICIENCY OF NUCLEIC ACID AMPLIFICATION REACTIONS WITH 3' MODIFIED OLIGONUCLEOTIDES

BACKGROUND OF THE INVENTION

1. Field of the Invention

This invention pertains generally to the field of molecular biology and particularly to techniques of primer dependent polymerase mediated DNA synthesis.

2. Description of Related Art

Relative Quantitative (RQ) RT-PCR™ ("reverse transcriptase—polymerase chain reaction") provides a reasonably accurate method of estimating relative levels of expression of individual genes between multiple samples.

To compensate for variations in RNA isolation, initial quantitation errors, and tube to tube variation in RT and PCR™ reactions, multiplex RT-PCR™ can be performed with an endogenous or exogenously added control amplicon. Multiplex RT-PCR™ with internal controls involves amplification using two PCR™ primer pairs in the same reaction to co-amplify two targets. One target is the sequence under study, the other is a fragment of an invariant sequence present in all samples. After the amplification reaction, PCR™ products are quantified and the yield of the target in each sample is adjusted up or down based on the variance in yield of the internal control amplified in each sample. In practice, this is specifically achieved by calculating the average yield of product per sample for the control product, then calculating the variance of the yield from the average for each individual sample, and finally, adjusting the yield of each experimental target by the inverse of the variance for the control in that sample.

In Competitive RT-PCR™, an exogenous target is added as an RNA template to the RT reaction. The level of sample to sample variation in target yield is then adjusted relative to the variation of the reference amplification product. Using an exogenously added standard has the advantage of giving the user absolute control over the amount of template added, with no variation between samples. Thus, the relative abundance of the control target should be adjusted to approximate that of the amplicon under evaluation. This is important because the control must be present in the RT-PCR™ at a level similar to the test transcript. If one target is present at a significantly higher concentration than the other, competition for reagents in the PCR™ will result in a loss of exponential amplification for the template of lower abundance. Because of competitive interference, the ability to obtain quantitative information will be lost. With this caveat in mind, any clone for which primers are available can be used as an exogenous standard as long as the PCR™ product can be differentiated from the experimental target or endogenous source of RNA homologous to the standard. RNA transcripts can be made by in vitro transcription and accurately quantified by including a trace amount of $^{32}$P-UTP in the reaction. A typical in vitro transcription reaction will produce enough RNA for thousands of RT-PCR™ reactions. If the first strand synthesis reaction is to be oligo dT-primed, the exogenous control transcript must include a poly (A) tail (as in a cDNA clone, for example). Using an exogenous standard requires considerably more effort compared to using an endogenous standard. Additionally, using such a standard does not control for differences in the quality of the starting RNA in the RT reaction. If there is a difference in the level of intactness of the RNA between otherwise identical samples, the yield of specific RT-PCR™ products will reflect this variation although the external standards will still look identical. For this reasons, as well as for simplicity and reproducibility, an endogenous RNA standard is preferred in Semi-Quantitative RT-PCR™.

In RQ RT-PCR™ product yields are normalized against internal, invariant controls (Horikoshi et al., 1992). The advantages of RQ RT-PCR™ over Competitive RT-PCR™ is that an exogenous standard is not required and multi-tube titration is not necessary for each sample once reasonable cycling conditions are established. However, the PCR™ must be terminated and analyzed while the reaction is in the linear phase for both the target and reference amplicon. This requires pilot experiments to determine cycling parameters designed to avoid plateaus in amplification and the subsequent careful quantitation of products.

Multiplex PCR™ is the simultaneous amplification of two or more nucleic acid fragments in the same PCR™ reaction. These fragments may be parts of different targets or contained in the same contiguous segment (i.e.: fragments of different genes or fragments of the same gene). Usually, multiple fragments are amplified with multiple PCR™ primer pairs. However, if the fragments share common sequences, they may be amplified using a single pair of PCR™ primers.

Theoretically, an ideal endogenous standard for RQ RT-PCR™ would be a transcript whose expression does not vary during the cell cycle, between cell types, or in response to the experimental treatments that one wishes to examine. Additionally, for an endogenous standard to be valid in multiplex PCR™ it is crucial that it be of a similar relative abundance as the target transcript. Unfortunately, such a molecule does not exist and there are serious limitations to the standards currently in use. For example, although β Actin is a frequently used standard (Horikoshi, et al. 1992; Gaudette and Crain, 1991), it's level of expression varies significantly from tissue to tissue. Additionally, co-amplification of an abundant transcript like β Actin or Glyceraldehyde-3-phosphate dehydrogenase (GAPDH) is a reasonable internal control only for transcripts of similar abundance.

Input RNA in RT-PCR™ reactions is usually quantified by spectrophotometer. The input RNA in a typical pre-PCR™ reverse transcription reaction is total RNA, quantified by absorbency at O.D.$_{260}$, 80% of which is ribosomal RNA. Furthermore the mRNA component of total cellular RNA can vary from 2% to 5% depending on the tissue. Therefore, even if a transcript was invariant (as expressed as a percentage of mRNA), it's relative abundance would still vary when considered as a percent of total input RNA from different source tissues. Since the majority of the RNA is rRNA, the level of rRNA remains essentially constant from sample to sample. Because 18S and 28S rRNA make up the majority of O.D.$_{260}$ absorbent material, they should make ideal invariant controls. In fact, 18S and 28S transcripts are frequently used as internal controls in Northern hybridization and RNAse protection assays. However, the abundance of rRNA has been a major limitation to it's utility as a control. For a control to be applicable for RQ RT-PCR™, it must be in the linear range of amplification under the same cycling conditions as the target under study (Ferre' et al., 1994). Thus rRNA has not previously proved useful as an RQ RT-PCR™ because it is thousands fold too abundant. Several partial solutions to this problem have been proposed, including using less input cDNA for abundant standards in separate PCR™ samples (Nicoletti and Sassy-Prigent, 1996) or introducing primers for abundant species at later cycles in the PCR™ (Wong et al., 1994). There are severe limitations to both these methods. The first method is not quantitative, and the second is unwieldy and laborious.

While PCR™ is the most often utilized method for the amplification of a specific nucleic acid sequence from a complex and often limited amount of starting nucleic acid, several isothermic amplification techniques may also be employed, and would benefit from the development of technologies which would enable the efficiency of a target amplicon to be altered without affecting other targets in a multiplex amplification reaction. Nucleic Acid Sequence Based Amplification (NASBA, Compton, 1991), Self-Sustained Sequence Based Amplification (3SR, Guatelli et al. 1990), and other closely related technologies amplify a specific target RNA sequence from a complex pool of nucleic acid sequences. Although these technologies are slightly different from each other, all rely on the coordinate activities of a retroviral reverse transcriptase and a bacteriophage RNA Polymerase. A hybrid oligonucleotide with a RNA polymerase promoter sequence at it's 5' end and a target specific sequence at it's 3' end is used as a primer by reverse transcriptase for cDNA synthesis. Reverse transcriptase then uses a second gene specific primer to make the cDNA double stranded. Next the phage promoter sequence (now double stranded) incorporated on the cDNA is used by the bacteriophage RNA polymerase for the synthesis of many RNA copies using the cDNA as template. These transcripts become substrates for reverse transcriptase and the cycle begins again. The advantages of isothermic RNA amplification as described is that thermal cycling is not required, the reaction is fast and (unlike in RT-PCR™) contaminating DNA cannot be used as template.

In International Patent WO94/03472, GenProbe describes a method for isothermic amplification of nucleic acid called Transcription Mediated Amplification (TMA). The amplification process described in the claim relies on reverse transcriptase (a primer dependent DNA polymerase) synthesizing cDNA, and RNA polymerase synthesizing RNA. The main amplification event is the RNA synthesis. Within the description of the technique, GenProbe describes the use of blocked or modified primers which are added to the reaction. These function to increase the specificity of the reaction by suppressing spurious side reactions such as primer-dimer formation. Nowhere in the reference is the use of blocked primers mentioned as a method to modulate the efficiency of DNA amplification. Additionally, the reference contains no mention of PCR™. The reference does describe ways to modify oligonucleotides. However, this is knowledge commonly known in the field.

SUMMARY OF THE INVENTION

The invention relates generally to methods of modulating the amplification efficiency of primer dependent polymerase mediated DNA synthesis with a blocked oligonucleotide primer that has been modified to prevent the primer from functioning in primer dependent polymerase mediated DNA synthesis. Such blocked oligonucleotide primers are also referred to as Competimers™.

In a specific embodiment, the invention contemplates the use of modified oligonucleotide primers with blocked 3' OH groups to adjust the amplification efficiency of an abundant target without affecting the amplification of other targets in a PCR™ reaction. By performing PCR™ with varying ratios of blocked oligonucleotides to PCR™ primers in the amplification reaction, the efficiency of the reaction can be predictably and reproducibly altered. Reducing the amplification efficiency of an abundant target in multiplex PCR™ has the effect of preserving relative sample to sample quantitative information for targets of vastly different abundance. However, the blocked primer technology is not limited to use in PCR™, but can be used in any primer dependent DNA transcription technology, such as reverse transcription or alternative amplification techniques such as NASBA, 3SR, or TMA.

Figure 1:
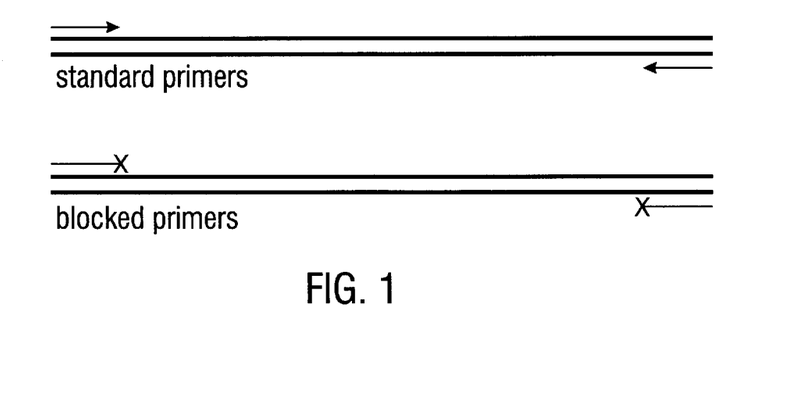
FIG. 1. Schematic of PCR™ with blocked primers.

The present invention allows the manipulation of the amplification efficiency of a PCR™ target without affecting relative quantitation or the amplification of other targets in a multiplex PCR™. This allows two targets of vastly different abundance to be quantified simultaneously in a multiplex RT-PCR™ reaction. This invention allows an invariant transcript of any relative abundance to be used as a control for any other transcript. The present invention is a method to perform PCR™ on an amplification target with two primer pairs of identical sequence, one of the pairs is modified to remove or block 3' terminal hydroxyl groups (FIG. 1). This modification may be via phosphorylation, biotinylation, or any modification to, or blocking of, the 3' OH to prevent a primer dependent DNA polymerase from initiating transcription off this primer. These blocked primers, or Competimers™ as the inventors refer to them, compete with the unmodified primers for binding to a DNA template but cannot be used as primers for extension by a DNA polymerase. Thus, at each extension step in PCR™, a percentage of template is unavailable for amplification. By increasing the ratio of Competimers™:primers in a PCR™, the amplification efficiency of an amplicon can be reduced so that the linear phase of accumulation of PCR™ product matches that of a less abundant target in multiplex PCR™.

Prior reports have described the use of primers with phosphorylated 3' OH groups in PCR™, but these are used in a PCR™ product detection technique known as TaqMan (Holland et al., 1991; Lee et al., 1993). The technique described in this report is the first which enables a scientist to reduce the amplification efficiency of a PCR™ reaction in a predictable, reproducible way. Equally important is the ability to modulate the efficiency of one amplicon in a multiplex PCR™ without affecting the efficiency of other amplicons in the same reaction.

The invention generally relates to method of using Competimers™. In a preferred embodiment, the invention contemplates methods of modulating the amplification efficiency of primer dependent polymerase mediated DNA synthesis comprising: (1) obtaining a DNA synthesis reaction mixture and (2) placing in the reaction mixture a Competimer™. The Competimer™ may have essentially the same sequence a primer employed in the synthesis reaction, but for a 3' terminal hydroxyl group of the Competimer™ has been modified in a manner that prevents the extension of the primer by DNA polymerase. A 3' terminal hydroxyl group of the Competimer™ may be modified by any number of means, for example, 3' addition of phosphate, biotin, digoxygenin, fluorescein, a dideoxynucleotide, an amine, a thiol, an azo ($N_3$) group, or fluorine. A Competimer™ may have a 3' terminal hydroxyl group that has been chemically modified. A Competimer™ may have a 3' terminal hydroxyl group that has been modified by biotinylation. A Competimer™ may have a 3' terminal hydroxyl group that has been modified by phosphorylation. A Competimer™ may have been modified by addition of a 3' terminal dideoxynucleotide.

A Competimer™ may be an RNA, DNA/RNA chimera, or PNA. A PNA is a peptide nucleic acid. These polymers have a peptide backbone instead of ribose and bind to nucleic acids of complementary sequence like an oligo.

However, they cannot function as primers for DNA polymerase and have a much higher Tm than DNA or RNA when duplexed with DNA. Thus, they can make even better Competimers™ than oligonucleotides. One major drawback to the use of PNA Competimers™ is expense.

The invention contemplates methods in which a Competimer™ is mixed in a ratio with an unblocked primer to modify the amplification efficiency of a target sequence in a primer dependent polymerase mediated DNA synthesis reaction. For example, the Competimer™ may be mixed in a ratio with the unblocked primer to modify the amplification efficiency of a target sequence in a PCR™ reaction. Alternatively, the Competimer™ is mixed in a ratio with the unblocked primer to modify the amplification efficiency of an RNA template in the RT-PCR™ reaction. The RNA template can be any suitable internal standard. For example, a suitable standard can be an 18S, 28S, or 5S ribosomal RNA, actin, or glyceraldehyde 3-P phosphate dehydrogenase RNA. The Competimer™ is typically mixed in a ratio with the unblocked primer to modify the amplification efficiency of a template in a RT-PCR™ reaction. In some embodiments, Competimer™ is longer or shorter in length than the unblocked primer. The DNA synthesis reaction may be a PCR™ reaction, and the amplification of an RNA target in the reaction may be modulated by addition of the Competimer™. Alternatively, the DNA synthesis reaction may be a nucleic acid sequence based amplification (NASBA), and the amplification of an RNA target in such a reaction may be modulated by addition of the Competimer™. Further, the DNA synthesis reaction may be a self sustained sequence amplification (3SR), and the amplification of an RNA target in the reaction may be modulated by addition of the blocked primer.

The invention also contemplates Competimers™ adapted to prevent primer dependent polymerase mediated DNA synthesis. In some preferred embodiments a 3' terminal hydroxyl group of the blocked oligonucleotide primer is modified in a manner that prevents the extension of the primer by DNA polymerase. This blocking can occur in any of the manners discussed above. The Competimer™ may be adapted to modify the amplification efficiency of a ribosomal RNA template in primer dependent polymerase mediated DNA synthesis reaction. For example, the Competimer™ may be adapted to modify the amplification efficiency of an 18S, 28S, or 5S ribosomal RNA template.

In a presently preferred embodiment, Competimer™ technology allows one to modulate the amplification efficiency of a PCR™ template without affecting the performance of other amplicons in a multiplex PCR™ reaction. In one specific embodiment of the invention, 18S rRNA Competimers™ allowing 18S rRNA to be used as an internal control for mRNAs of any abundance. The 18S rRNA primers and Competimers™ may be supplied separately as 5 uM stocks of forward and reverse primers mixed in a 1:1 ratio. The 18S Competimers™ may be identical in sequence to the 18S PCR™ primers, but modified at their 3' ends to block extension by DNA polymerase. By mixing primers with increasing amounts of Competimers™, the overall amplification efficiency of the PCR™ is reduced, without primers becoming limiting or the loss of relative quantitation. As a general guideline, the more rare a PCR™ target, the higher a Competimer™ ratio needed. When experimental targets are extremely rare in abundance, nested PCR™ is usually employed. This involves performing PCR™, removing a small aliquot of the reaction, and performing a second round of PCR™ on this sample. In situations such as these, the 18S primers and Competimers™ are added only to the second PCR™ reaction. This has the effect of further lowering the overall amplification efficiency of the 18S amplicon relative to the rare target. However, this has no detrimental effect on the performance of the 18S target as an endogenous control. To enhance their versatility, 18S rRNA primers may be designed to function with RNA from all vertebrates and to organisms as distant as yeast. The inventors have tested one such Competimer's™ ability to function in RT-PCR™ with cDNA made from human, rat, hamster, mouse, chicken, zebrafish, Xenopus, and Drosophila RNA.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

EXAMPLE 1

Standard RT Reaction

Unless otherwise noted, the reverse transcriptase reactions performed in the studies described in these illustrative embodiments were carried out under the following conditions. 1 ng–1 µg total mouse liver RNA (variable), 500 µM dNTPs, 250 ng random decamer primer, 10 mM Tris-Cl pH 8.3, 50 mM KCl, 1.5 mM MgCl$_2$, Placental RNAse Inhibitor (Ambion) 1 unit, Molony Murine Leukemia Virus (MuLV) Reverse Transcriptase (Ambion) 100 units, were placed in a 20 µl reaction volume.

The reactions were incubated at 42° C. for 60 minutes, terminated by heating at 95° C. 5 minutes.

EXAMPLE 2

Standard PCR™ Reaction

Unless otherwise noted, the PCR™ reactions performed in the studies described in these illustrative embodiments were carried out under the following conditions. 1 µl reverse transcription reaction, 200 µM dNTPs, 400 nM each PCR™ primer, 1 unit Taq Polymerase (Takara), 10 mM Tris-Cl pH 8.3, 50 mM KCl, 1.5 mM MgCl$_2$ in a reaction volume of 50 µl.

PCR™ cycling conditions were: initial denaturation at 94° C. for 3 minutes. 26 or 30 cycles of 94° C. 30 seconds, 57° C. 30 seconds, 72° C. 30 seconds, then a final extension 5 minutes at 72° C.

PCR™ products are analyzed by agarose gel electrophoresis on a 4% gel with 1 µg/ml ethidium bromide and photographed under 300 nm U.V. light.

EXAMPLE 3

Adaptation of 18S rRNA as an Internal Control in Relative RT-PCR™

Taq DNA polymerase depends upon the presence of a free hydroxyl group on carbon 3 of the deoxyribose ring on the 3' end of a oligonucleotide primer to successfully initiate DNA synthesis. In a PCR™ reaction, where template is limiting, and primers are in excess, the inclusion of primers with blocked 3' OH groups has the effect of reducing the effective concentration of available targets for Taq polymerase to amplify.

Figure 2:
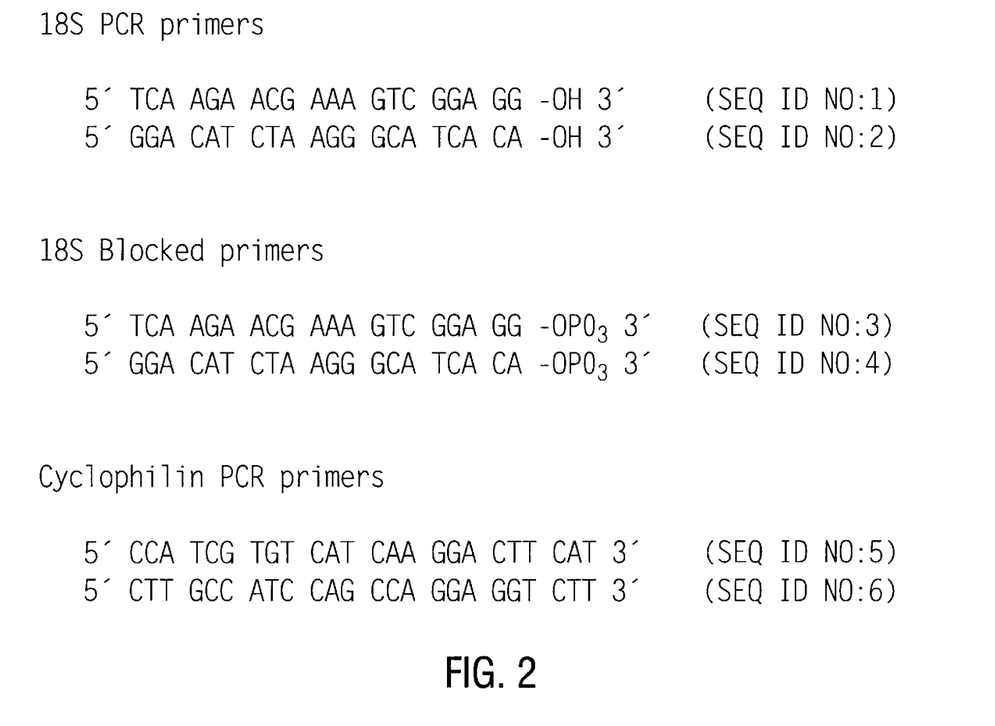
FIG. 2. Diagram showing 18S PCR™ primers (SEQ ID NOS: 1 & 2), 18S blocked primers (SEQ ID NOS: 3 & 4), and Cyclophilin PCR™ primers (SEQ ID NOS: 5 & 6).

The practicality of this invention is demonstrated by the adaptation of the 18S rRNA transcript as an endogenous control in RQ RT-PCR™ for mouse Cyclophilin, a target of vastly lower relative abundance. PCR™ primers for 18S rRNA and Cyclophilin are described in FIG. 2.

Figure 3:
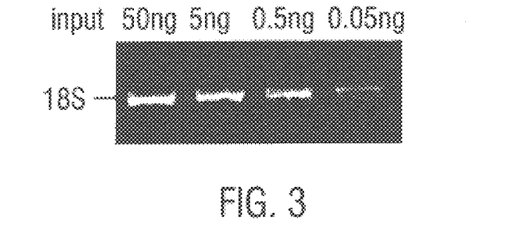
FIG. 3 (Scanned image) RT-PCR™ of 18S, with log dilutions of input total RNA.

18S ribosomal RNA represents approximately 30% of total cellular RNA. Because of it's high relative abundance, amplification of 18S rRNA using RT-PCR™ conditions designed for moderately expressed mRNA transcripts quickly saturates a PCR™ reaction with 18S rRNA product. For example, the inventors performed PCR™ of 18S rRNA from cDNA synthesized from four reverse transcription reactions using 0.05 nanograms (ng), 0.5 ng, 5 ng, and 50 ng of total cellular RNA. 4 standard RT reactions were performed as described earlier: input RNA was total mouse liver RNA, amount varied as follows: tube 1: 1 $\mu$g, tube 2: 100 ng, tube 3: 10 ng, tube 4: 1 ng. One $\mu$l of each RT reaction was subject to PCR™ for 30 cycles under standard conditions and a 10 $\mu$l aliquot of each PCR™ was assayed by gel electrophoresis as described above. As shown in FIG. 3, the yield of 18S product is only proportional to input RNA over the range of 0.05 ng–0.5 ng (0.5–5 cell-equivalents).

Figure 4:
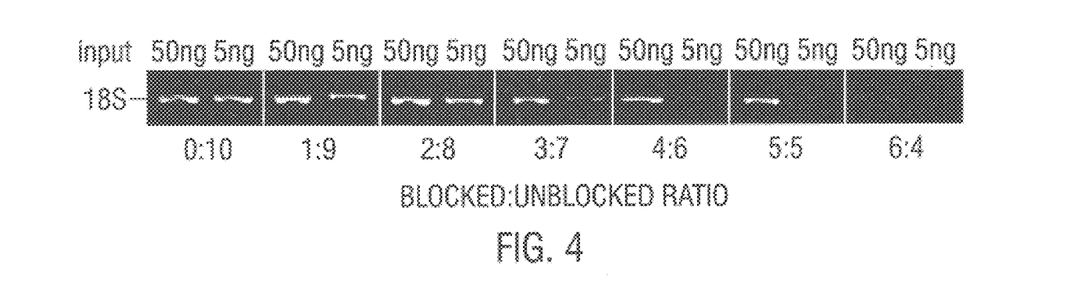
FIG. 4 (Scanned image) RT-PCR™ of 18S on 2 concentrations of input total RNA using increasing 18S Competimer™:primer ratios.

However, in a series of reactions under identical conditions but with increasing ratios of 18S Competimer™ primers, 2 identical RT reactions were performed using standard reaction conditions. Input RNA was total mouse liver RNA. Tube A: 1 $\mu$g, tube B: 100 ng. 14 standard PCR™ reactions were assembled, labeled 1A–7A and 1B–7B. 1 $\mu$l of the tube A RT was added to each of the A tubes. 1 $\mu$l of the tube B RT was added to each of the B tubes. The total oligonucleotide concentration in these PCR™ reactions was as described above, however the composition of the primers in each of the 7 pairs of tubes varied as follows: Tubes 1A and B, 100% 18S primers, tubes 2A and B: 90% 18S:10% Competimers™, tubes 3A and B 80% 18S:20% Competimers™, tubes 4A and B: 70% 18S:30% Competimers™, tubes 5A and B: 60% 18S:40% Competimers™, tubes 6A and B 50% 18S:50% Competimers™, tubes 7A and B 40% 18S:60% Competimers™. Standard cycling conditions were performed for 30 cycles and analyzed by gel electrophoresis as described above.

In the study shown in FIG. 4, the absolute yield of PCR™ product is reduced, but the relative ratio of input to output is restored. (FIG. 4). This represents a 100-fold shift in the level of input cDNA which results in linear accumulation under identical cycling conditions. This effect is not simply due to the primers being in limiting amounts, since that would result in premature termination of amplification and identical yields in all samples.

Attenuation of product yield is far less than expected if the Competimers™ were 100% effective at blocking amplification. For example, if a 1:1 Competimer™:primer ratio lowered efficiency by 50%, there should be a several-log fold reduction in product yield. The inventors speculate that there is a dynamic exchange of primers on the amplification template during the annealing/extension phase of the PCR™ cycle. Thus, blocked primers only decrease the percentage of time an individual template will have a unblocked primer in position for extension. This theory is supported by the inventors' observation that the relative length of the blocked oligonucleotides affect their 'potency' as modulators of PCR™ efficiency. Blocked oligonucleotides which are longer than their PCR™ counterparts are more potent inhibitors than are shorter ones. Therefore, an important variable in the dynamics of the system is the thermodynamic stability of the blocked oligonucleotide versus the PCR™ primer when annealed to a PCR™ template.

EXAMPLE 4

Multiplex RT-PCR™ of Cyclophilin A With 18S Competimers™

Additional studies illustrate the usefulness of the invention and how it can enable 18S rRNA to be used as a control. These studies involved multiplex RT-PCR™ for Cyclophilin, a moderately expressed mRNA transcript.

Initially, RT-PCR™ conditions were established that would result in PCR™ products being in a linear range for Cyclophilin. To do this, a standard reverse transcription may be performed using 1 $\mu$g input RNA. This cDNA sample can then be diluted by log dilutions, such that 5 additional samples are produced: these are dilutions of $10^{-1}$, $10^{-2}$, $10^{-3}$, $10^{-4}$, and $10^{-5}$. Then 6, or a relevant number, PCR™ reactions may be performed using standard conditions with 1 $\mu$l of each of these log dilutions as input cDNA. There should be at least two data points where the amount of product produced is proportional to the input cDNA (e.g. 10× more product from 10× more input cDNA). Use this range of amount of RT input in future PCR™ reactions. In the present example, the conditions used are 26 cycles of PCR™ on 1 $\mu$l undiluted RT and 1 $\mu$l of a 10 fold dilution.

Figure 5:
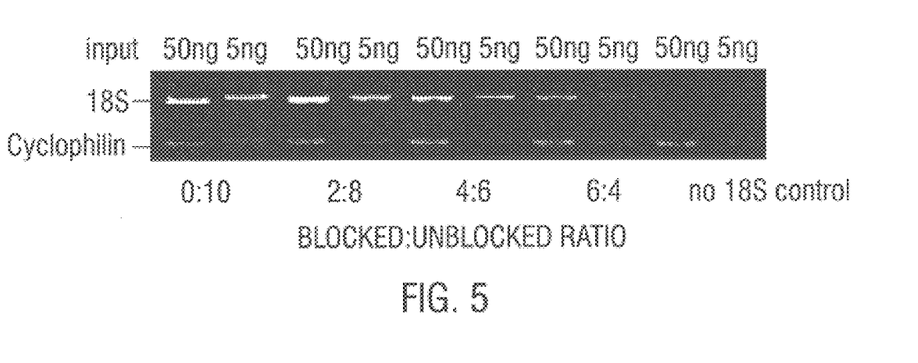
FIG. 5 (Scanned image) Multiplex RT-PCR™ of Cyclophilin A with 18S Competimers™ on two concentrations of input total RNA using increasing 18S Competimer™:primer ratios.

Using these cycling conditions, the inventors performed multiplex PCR™ on similar samples with Cyclophilin primers and varying ratios of 18S Competimer™:primer mixes. To determine the appropriate mix of 18S primers/Competimers™ to use in multiplex PCR™ with mouse Cyclophilin, a series of pilot reactions was performed using the cyclophilin reaction conditions determined above. 5 identical pairs of PCR™ reactions were assembled using the standard reaction conditions and a pair of cyclophilin PCR™ primers at 0.5 $\mu$M. Tube one of each pair had 1 $\mu$l of a 1 $\mu$g reverse transcription reaction as template, tube 2 of each pair had 1 $\mu$l of a 100 ng reverse transcription reaction as template. To pair one, standard 18S primers were added. To pair two, a mixture of 80% primers:20% competimers™ was added. To pair three, 60% primers:40% Competimers™. To pair four, 40% primers:60% Competimers™. Pair five was a control, with no 18S oligonucleotides added. After standard cycling for 26 cycles, these samples were analyzed by gel electophoresis.

FIG. 5 is an agarose gel of the multiplex RT-PCR™ of Cyclophilin co-amplified with 18S rRNA. Several conclusions can be drawn from the analysis of the data. First, under these cycling conditions, amplification of Cyclophilin from these cDNA reactions is in linear range (compare odd and even numbered samples). Second, co-amplifying 18S rRNA with Cyclophilin does not affect the yield of the Cyclophilin product (compare samples 9 and 10, amplified with no 18S primers to samples 1 and 2, amplified with unblocked 18S primers). Third, without the use of Competimers™, the yield of 18S product is not proportional to input cDNA (lanes 1 and 2 do not have 1× and 10× amounts of 18S product). And finally, as the Competimer™ ratio is increased to 6:4, the 18S product becomes proportional to input cDNA (compare the 18S product in lanes 7 and 8). Thus for RQ RT-PCR™ of the Cyclophilin transcript, a 6:4 ratio of 18S Competimers™:primers allows simultaneous relative quantitation of these two transcripts. For simultaneous quantitation of 18S with a transcript of lower relative abundance than Cyclophilin, a higher ratio of Competimers™ must be used to further reduce the efficiency of 18S amplification.

EXAMPLE 5

Standard Protocol for RT-PCR™ Using Competimers™

For reproducible Relative RT-PCR™, it is typical to empirically determine reaction conditions and cycling parameters that will result in a reaction that is terminated during the exponential phase of amplification for the amplicon of interest. If total RNA is not limiting, a good starting point is the standard RT reaction as described above with 1 μg input RNA. However, the amount of RT reaction added to the PCR™ can be varied from 0.001 μg to 5 μg and the effects on the PCR™ can be assessed by gel electrophoresis. To analyze multiple targets by relative quantitative RT-PCR™, cycling parameters that meet this criteria ere determined separately for each before co-amplification is attempted. To determine conditions for RT-PCR™ of each template of unknown abundance, one may use standard reaction conditions for PCR™ while varying the input cDNA from a single 1 μg RT reaction diluted over several log dilutions. Analysis the products can be done by gel electrophoresis. There should be at least two data points where the amount of product produced is proportional to input cDNA for each target (e.g. 10× more product from 10× more input cDNA). Use this range of cDNA input in future PCR™ reactions. If the working dilution is more than 1:10, the amount of input RNA into subsequent RT reactions may be reduced to save material and the calibration study repeated.

If the range for linear amplification of two targets is more than two logs different, then they cannot be co-amplified. This is because the more abundant target (or the one than amplifies more efficiently) will out-compete the less abundant for limiting reagents causing a failure of amplification of the less abundant target. This limitation can be overcome by using of Competimers™ to lower the amplification efficiency of the more abundant target. Once specific PCR™ primers are chosen, the Competimers™ can be designed to the same sequence. Several different 3' modifications can be inexpensively added during synthesis by commercial oligonucleotide suppliers. These include substituting a dideoxynucleotide on the 3' end of an oligonucleotide, 3' phosphorylation, or addition of a detection molecule such as biotin, digoxygenin, or fluorescein on the 3' terminal hydroxyl group. Any of these modifications will prevent the oligonucleotide from functioning as a primer for a DNA polymerase. Most, if not all oligonucleotide synthesis companies offer these modifications, such as Genosys Biotechnologies, IDT, and The Great American Gene Company.

Steps of a pilot study are as follows:

(1) Prepare pilot mixes of PCR™ primers/Competimers™ for the abundant target:

| mix: | 1:9 | 3:7 | 5:5 | 7:3 | 9:1 |
|---|---|---|---|---|---|
| Competimers ™ (μl) | 1 | 3 | 5 | 7 | 9 |
| primers (μl) | 9 | 7 | 5 | 3 | 1 |

(2) Make a standard PCR™ cocktail for 10 identical samples as follows:

| | |
|---|---|
| 50 μl | 10X PCR ™ buffer (100 mM Tris-Cl pH 8.3, 500 mM KCl, 15 mM MgCl$_2$) |
| 40 μl | 2.5 mM dNTPS |
| 25 μl | target PCR ™ primer pair (5 μM) |
| 2.0 μl | thermophilic Polymerase |
| 355.5 μl | H$_2$O |

(3) Split into two cocktails (a) and (b) of 240 μl each.

(4) To cocktail (a) add 5 μl of RT reaction (using the range of input RT determined above for the less abundant target) and 0 μl H$_2$O.

(5) To cocktail (b) add 0.5 μl of RT reaction (using the range of input RT determined above for the less abundant target) and 4.5 μl H$_2$O.

(6) Label 10 tubes 1a, 1b–5a and 5b.

(7) To tubes # 1a and 1b, add the a or b cocktail but no primer/Competimer™ mix. These samples control for efficiency of amplification of the less abundant amplicon alone. To the subsequent tubes, add 4 μl of one of the primer/Competimers™ mixes and 46 μl of the appropriate (a) or (b) PCR™ cocktail. Perform the standard PCR™ and assess the results by gel electrophoresis.

A successful study should meet several criteria. First, addition of the second set of primers and amplification of the second target should not affect the yield of the co-amplified target. If it does, either the number of cycles need to be reduced because reagents are severely limiting or the second primer pair is interfering with the function of the first primer pair.

Primer design computer software, such as Oligo5.0 or PrimerSelect should be used to insure that the primers do not have significant homology to interfere with each other in PCR™.

As the ratio of Competimers™ to primers increase, the overall efficiency of amplification of the more abundant target should decrease. Simultaneously, the relative amount of 18S product produced in A and B samples increase to the desired 10:1 ratio. As the ratio of Competimers™ increases further, this relative quantitation is preserved, but the yield continues to decrease. The Competimer™:primer ratio best suited to a particular pair of PCR™ targets is the one with the lowest ratio of Competimers™ which yields quantitative information and overall yield for the more abundant target roughly equivalent to the less abundant amplicon under study.

EXAMPLE 6

Standard Protocol for NASBA and 3SR Using Competimers™

As described earlier, several similar isothermic amplification techniques depend on a pair of gene specific primers for reverse transcription and amplification of RNA. While these reactions are relatively robust, there is a critical weakness inherent to the technology. Whereas relative quantitative multiplex PCR™ is readily achievable by someone moderately skilled in the art, isothermic amplification reactions are recalcitrant to multiplex reactions: small, unpredictable differences in transcriptional efficiency result in large differences in product yield. Until the development of the blocked primer technology presented in this application, there was no generally applicable solution to this problem. The use of blocked primers allow the modulation of the first steps in the isothermic amplification reaction, namely the reverse transcription of target into double stranded cDNA by the primer-dependent reverse transcriptase.

Representative protocol for using blocked primers in isothermic RNA transcription based amplification: modification of the Self-Sustained Sequence Amplification (3SR) protocol published by Guatelli et al. (1990). Adaptation of Competimer™ technology to other isothermal transcription based amplification technologies following the teachings of this specification are within the abilities of one skilled in the art.

General 3SR Reaction Conditions 40 mM Tris-Cl pH 8.1, 20 mM $MgCl_2$, 25 mM NaCl, 2 mM spermidine hydrochloride, 5 mM dithiotreitol, bovine serum albumin (80 µg/ml), 1 mM dNTPs, 4 mM rNTPs, 250 ng T7 promoter/gene-specific chimeric downstream oligonucleotide, 250 ng gene specific upstream oligonucleotide, 30 units AMV reverse transcriptase, 100 units T7 RNA polymerase, 4 units RNAse H, and template RNA in a final volume of 100 µl, incubated at 37° C. for 1 hour. Products are electrophoresed on 5% polyacrylamide/ 7M urea denaturing gels, stained with 1 µg/ml ethidium bromide and visualized under 300 nm ultraviolet light.

After establishing that primer pairs for individual targets function in individual 3SR reactions, both pairs of primers are added to a single reaction. The products are evaluated by gel electrophoresis as described above. If the amplified products are present at grossly different levels, sample to sample quantitation will not be possible. Since one amplicon is amplified to the detriment of the other, the yield of the less efficient target will not be proportional to input RNA when multiple samples are assayed. By titering in Competimers™ for the more abundantly produced target, the amplification efficiency of this target will be lowered to produce equivalent amounts of both products. Multiplex relative quantitative analysis can then be performed on multiple RNA samples. The majority of the amplification in transcription based isothermal amplification takes place in the primer independent RNA polymerase step. Thus to achieve the desired effect, Competimers™ must be titered in over a broader range and higher ratio than used in PCR™.

Calibration Protocol for Competimers™ in the 3SR Reaction

Establish input RNA levels that result in quantitative output. Set up 3SR reactions with log dilutions of input RNA. For example: 1 µg 100 ng 10 ng 1 ng 10 pg 10 pg 1 pg. Perform the reactions with each primer pair for the two genes of interest in separate 3SSR reactions. One of the two targets amplified could be 18S rRNA as an internal standard, or a second gene of interest. Analyze the products on a page/urea gel. Determine which target is amplified at lower abundance and determine the dilution range of RNA yields product proportional to input.

Make mixtures of the primer pair and Competimers™ for the more highly amplified target:

Competimer™:primer pair ratio (total concentration 250 ng 5' and 250 ng 3'/µl)

0.5:9.5, 1:9, 1.5:8.5, 2:8, 2.5:7.5, 3:7, 3.5:6.5, 4:6, 4.5:5.5, 5:5.

Set up a cocktail for twenty 3 SR reactions as described above, including the primers for the target amplified at lower efficiency. Label reaction tubes 1A–10A and 1B–10B. Chose two log dilutions of RNA that produced proportional product as determined above. Add the 1× sample to the A tubes, the 10× sample to the B tubes. To both A and B series, add the Competimer™:primer mixes, such that tubes 1A and 1B receive the 0.5:9.5 mix. Tubes 2A and B receive the 1:9 mix, etc. Perform the 3SR reactions and analyze samples as described above. As the ratio of Competimers™ increase, the overall efficiency of amplification of the more abundant target decreases. There should be at least one set of conditions in which both targets are amplified to approximately equal levels and the yield in the 1× samples is ten fold less than that in the 10× samples. This can be estimated by loading 10 fold less than the 10× samples on a gel next to an aliquot of the 1× reaction. For future analysis, use the range of input RNA and the ratio of Competimers™ determined from these preliminary studies.

EXAMPLE 7

Using Blocked Primers for Multiplex Fluorescent In-Situ PCR™

Localization of 2 different RNA transcripts in the same tissue section can be accomplished by incorporating different fluorescent dyes in PCR™ primers for the two different targets. However, if the targets are of vastly different abundance, the rarer may not be PCR™ amplified to detectable levels. Co-localization of targets with vastly different relative abundance can be accomplished in the same tissue section by in situ PCR™ using blocked primer technology. For example, during heart development in Xenopus, a number of cardiac specific markers are transcribed. Some of these, like Cardiac Troponin are abundantly expressed, while others such as Xnkx-2.5 are very rare. By performing multiplex RT-PCR™ with PCR™ primers for both genes and blocked primers for the more abundant transcript, both products can be successfully amplified and visualized in the same section.

In Situ RT-PCR™, a method for detecting a RNA transcript in a tissue sample by RT-PCR™ is a still-developing technology. The basic protocol for in situ RT-PCR™ is the same as for the standard protocol, with the exception of having to perform the reaction on tissue sections affixed to microscope slides. The technical aspects unique to in situ RT-PCR™ are described in detail in a previous publication (PCR™ In Situ Hybridization, Gerald Nuovo ed., Raven Press). Because of current limitations in technology, only one target is amplified per reaction. However, as the technology becomes more widely used, multiplex RT-PCR™ will be more commonly utilized. The advantage of multiplex in situ RT-PCR™ is the ability to determine if different RNA transcripts are expressed in the same cell, or whether their pattern of expression is different among cells of the same tissue. Simultaneous detection of two amplified targets by microscopy requires a hybridization and detection step with probes that fluoresce with different wavelengths so that the different products can be distinguished from each other. However, the limitations of multiplex in situ RT-PCR™ are the same as standard multiplex RT-PCR™, that is if one target is much more abundant or is amplified at much higher efficiency, the second target may not be detectable. This limitation can be overcome by using of Competimers™ to lower the amplification efficiency of the more abundant target. Once specific PCR™ primers are chosen, Competimers™ can be designed to the same sequence.

Pilot study for calibrating Competimers™ in multiplex in situ RT-PCR™:

Prepare mixes of PCR™ primers/Competimers™ for the abundant target:

| mix: | 1:9 | 3:7 | 5:5 | 7:3 | 9:1 |
|---|---|---|---|---|---|
| Competimers ™ (µl) | 10 | 30 | 50 | 70 | 90 |
| primers (µl) | 90 | 70 | 50 | 30 | 10 |

Make a standard PCR™ cocktail for 5 identical 100 µl samples as follows:

| | |
|---|---|
| 10X PCR ™ buffer | 50 µl |
| (100 mM Tris-Cl pH 8.3, 500 mM KCl, 15 mM MgCl₂) | 40 µl |
| 2.5 mM dNTPS | |
| less abundant PCR ™ primer pair (5 µM) | 25 µl |
| thermophilic Polymerase | 2.0 µl |
| H₂O | 355.5 µl | split cocktail into 5 samples and add one of the primer:Competimer™ mixes to each sample. Hybridize each probe to two serial sections of target tissue and follow through with the detection protocol for each probe separately on one of the two sections. A successful study should meet several criteria. As the ratio of Competimers™ increases, the signal level for the abundant target should be reduced. The proper Competimer™ ratio to use for future multiplex studies is one in which both targets are amplified and detected to approximately equal levels.

EXAMPLE 8

Manufacture of Competimers™

Competimers™, by definition, are modified oligonucleotides which do not have free 3' hydroxyl groups and which compete with unmodified oligonucleotide primers for binding sites on nucleic acid molecules. Such competition, if it occurs during a primer extension reaction like PCR™ or reverse transcription decreases the chance of the DNA polymerase finding a primer in place on the template, and thus lowers the efficiency of the reaction. Oligonucleotides are synthesized on automated machines from the 3' to the 5' direction, with the 3' base supplied coupled to the controlled pore glass (cpg) synthesis column. Modifications to the 3' end, such as phosphorylation, biotin, amine, sulfhydryl, fluorescein are also supplied attached to the 3' hydroxyl on the column as purchased. A dideoxynucleotide may also be substituted for a deoxynucleotide at the 3' end already attached to the column. Thus, it simply a matter of substituting one disposable synthesis column for another to synthesize a Competimer™, easily accomplished by anyone skilled in the art of oligonucleotide synthesis and available from any commercial service which offers custom oligonucleotide synthesis. Examples of such suppliers are Genosys Biotechnologies (800) 234-5362, DNA Technologies (800) 998-3628, Midland Reagents (800) 247-8766 and Ransom Hill (800) 597-8509.

Parameters that determine the 'potency' of a Competimer™ appears to be the stability of the duplex of the Competimer™ and the oligonucleotide primer and the target. Thus, if the Competimer™ is longer at the 5' end than the primer, it forms a more stable duplex with the target than the primer and target. This results in a stronger effect on amplification efficiency for a given ratio of Competimer™:primer. One could take advantage of this knowledge to design very effective Competimers™ using PNA (protein nucleic acid). These molecules, commercially synthesized, have protein backbones instead of ribose backbones and form PNA/DNA hybrids which have much greater stability than the equivalent DNA/DNA hybrid. The extra cost incurred because of higher synthesis costs may be offset by the gain in effectiveness of these Competimers™.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Compton, "Nucleic acid sequence-based amplification," *Nature*, 350:91–92, 1991.

Ferre F, Marchese A, Pezzoli S, Griffin, Buxton E, and Boyer, V, *Quantitative PCR™; An Overview in The Polymerase Chain Reaction*, Mullis, Ferre', and Gibbs, eds., 66–109, 1994.

Gaudette M F, and Crain W R, "A simple method for quantifying specific mRNAs in small numbers of early mouse embryos," *Nucleic Acids Res*, 19:8:1879–1884, 1991.

Guatelli, Whitfield, Kwoh, Barringer, Richman, and Gingeras, "Isothermal in vitro amplification of nucleic acids by a multienzyme reaction modeled after retroviral replication," *PNAS*, 87:1874–1878, 1990.

Holland P M, Abramson R D, Watson R, and Gelfand D H., "Detection of specific polymerase chain reaction product by utilizing the 5'→3' exonuclease activity of *Thermus Aquaticus* DNA polymerase," *Proc. Natl. Acad. Sci. USA*, 88:7276–7280, 1991.

Horikoshi T, Danenberg K D, Stadlbauer T H W, Volkenandt M, Shea, L C C, Aigner K, Gustavsson B, Leichman L, Frosing R, Ray M, Gibson N W, Spears C P, and Danenberg P V., "Quantitation of thymidylate synthesis, dihydrofolate reductase, and DT-diaphorase gene expression in human tumors using the polymerase chain reaction," *Cancer Research*, 52:108–116, 1992.

Lee L G, Connell C R, and Bloch W., "Allelic discrimination by nick-translation PCR™ with fluorogenic probes," *Nucl. Acids Res.*, 21:3761–3766, 1993.

Nicoletti A, and Sassy-Prigent C., "An alternative quantitative polymerase chain reaction method," *Anal Biochem*, 236:229–241, 1996.

Wong H, Anderson W D, Cheng T, and Riabowol KT, "Monitoring mRNA expression by polymerase chain reaction: The 'primer-dropping' method." *Anal Biochem*, 223:251–258, 1994.

What is claimed is:

1. A method of modulating the amplification efficiency of a target sequence in a multiplex thermal cycling, primer dependent polymerase mediated DNA synthesis comprising:

obtaining a multiplex thermal cycling, primer dependent polymerase DNA synthesis reaction mixture, comprising one or more unblocked primer pairs effective to amplify multiple target sequences; and placing one or more modified primer in the reaction mixture;

wherein said one or more modified primer competes with said one or more unblocked primer for hybridization to a target sequence and wherein said one or more modified primer is modified to prevent the modified primer from functioning in primer dependent polymerase mediated DNA synthesis, and further wherein said modulating is dependent on the ratio of said unblocked primer to said modified primer.

2. The method of claim 1, wherein a 3' terminal hydroxyl group of said one or more modified primer has been modified in a manner that prevents the extension of the modified primer by DNA polymerase.

3. The method of claim 1, wherein a 3' terminal hydroxyl group of said one or more modified primer has been modified by 3' addition of phosphate, biotin, digoxygenin, fluorescein, a dideoxynucleotide, an amine, a thiol, an azo ($N_3$) group, or fluorine.

4. The method of claim 1, wherein a 3' terminal hydroxyl group of said one or more modified primer has been chemically modified.

5. The method of claim 1, wherein a 3' terminal hydroxyl group of said one or more modified primer has been modified by biotinylation.

6. The method of claim 1, wherein a 3' terminal hydroxyl group of said one or more modified primer has been modified by phosphorylation.

7. The method of claim 1, wherein said one or more modified primer has been modified by addition of a 3' terminal dideoxynucleotide.

8. The method of claim 1, wherein said one or more modified primer is an RNA, or a DNA/RNA chimera.

9. The method of claim 1, wherein said one or more modified primer is mixed in a ratio with the unblocked primer to modify the amplification efficiency of an RNA template in the RT-PCR™ reaction.

10. The method of claim 9, wherein the RNA template is an 18S, 28S, or 5S ribosomal, actin, or glyceraldehyde 3-P phosphate dehydrogenase template.

11. The method of claim 9, wherein the RNA template is an 18S ribosomal template.

12. The method of claim 1, wherein said one or more modified primer is mixed in a ratio with the unblocked primer to modify the amplification efficiency of a template in a RT-PCR™ reaction.

13. The method of claim 1, wherein said one or more modified primer is longer or shorter in length than the unblocked primer.

14. The method of claim 1, wherein the DNA synthesis reaction is a PCR™ reaction, and the amplification of an RNA target in the reaction is modulated by addition of said one or more modified primer.

15. The method of claim 1, wherein the amplification of said target sequence is modulated without affecting the efficiency of amplification of other sequences in said multiplex thermal cycling, primer dependent polymerase DNA synthesis.

16. The method of claim 15, wherein said target sequence is an internal standard and said amplification is modulated to maintain the amplification of said internal standard in the linear range concurrently with linear amplification of one or more of said other target sequences in said multiplex thermal cycling, primer dependent polymerase DNA synthesis.

17. The method of claim 16, wherein said target sequence is an endogenous RNA standard in a Semi-Quantitative RT-PCR™.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:1:

TCAAGAACGA AAGTCGGAGG                                      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:2:

GGACATCTAA GGGCATCACA                                      20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:3:

TCAAGAACGA AAGTCGGAGG                                      20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (xi) SEQUENCE DESCRIPTION: SEQ ID NO:4:

GGACATCTAA GGGCATCACA                                      20

(2) INFORMATION FOR SEQ ID NO:5:

(i) SEQUENCE CHARACTERISTICS:
      (A) LENGTH: 24 base pairs
      (B) TYPE: nucleic acid
      (C) STRANDEDNESS: single
      (D) TOPOLOGY: linear    (xi) SEQUENCE DESCRIPTION: SEQ ID NO:5:

CCATCGTGTC ATCAAGGACT TCAT                                  24

(2) INFORMATION FOR SEQ ID NO:6:

-continued

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:6:

CTTGCCATCC AGCCAGGAGG TCTT                                              24
```